US008273376B2

(12) United States Patent
Andremont et al.

(10) Patent No.: US 8,273,376 B2
(45) Date of Patent: Sep. 25, 2012

(54) COLONIC DELIVERY OF METALLO-DEPENDENT ENZYMES

(75) Inventors: Antoine Andremont, Malakoff (FR); Helene Huguet, Paris (FR)

(73) Assignees: DA Volterra, Paris (FR); Assistance Publique-Hopitaux de Paris, Paris (FR); Universite Paris Diderot-Paris 7, Paris (FR)

( * ) Notice: Subject to any disclaimer, the term of this patent is extended or adjusted under 35 U.S.C. 154(b) by 580 days.

(21) Appl. No.: 11/985,411

(22) Filed: Nov. 15, 2007

(65) Prior Publication Data

US 2008/0199528 A1    Aug. 21, 2008

Related U.S. Application Data

(60) Provisional application No. 60/859,599, filed on Nov. 17, 2006.

(51) Int. Cl.
*A61K 9/50* (2006.01)
(52) U.S. Cl. ........................ 424/497; 424/94.3; 424/94.6
(58) Field of Classification Search ........................ None
See application file for complete search history.

(56) References Cited

U.S. PATENT DOCUMENTS

| | | | |
|---|---|---|---|
| 3,959,457 A | 5/1976 | Speaker et al. | |
| 5,051,304 A | 9/1991 | David et al. | |
| 5,607,671 A | 3/1997 | Heino | |
| 5,700,459 A | 12/1997 | Krone et al. | |
| 6,436,461 B1 | 8/2002 | Bouwmeesters et al. | |
| 6,500,423 B2 | 12/2002 | Olshenitsky et al. | |
| 6,531,152 B1 | 3/2003 | Lerner et al. | |
| 6,632,451 B2 | 10/2003 | Penhasi et al. | |
| 2004/0067223 A1 | 4/2004 | Jacob et al. | |
| 2005/0249716 A1 | 11/2005 | Bourgeois et al. | |
| 2008/0031867 A1 | 2/2008 | Huguet et al. | |
| 2008/0124279 A1 | 5/2008 | Andremont et al. | |
| 2009/0324568 A1 | 12/2009 | Huguet et al. | |

FOREIGN PATENT DOCUMENTS

| | | |
|---|---|---|
| EP | 0 213 303 A2 | 3/1987 |
| EP | 0 273 823 A1 | 7/1988 |
| EP | 0 338 499 A2 | 10/1989 |
| EP | 0 454 044 A2 | 10/1991 |
| EP | 0 480 729 A1 | 4/1992 |
| FR | 2 843 301 A1 | 2/2004 |
| JP | 04-013724 A | 1/1992 |
| WO | WO-88/07865 A1 | 10/1988 |
| WO | WO-92/00732 A1 | 1/1992 |
| WO | WO-93/13757 A1 | 7/1993 |
| WO | WO-95/05939 A1 | 3/1995 |
| WO | WO-97/25979 A1 | 7/1997 |
| WO | WO-97/27843 A2 | 8/1997 |
| WO | WO-98/15192 A1 | 4/1998 |
| WO | WO-2004/016248 A2 | 2/2004 |
| WO | WO-2005/092295 A1 | 10/2005 |
| WO | WO-2006/122835 A1 | 11/2006 |

OTHER PUBLICATIONS

Bourgeois et al., Journal of Drug Targeting, Jun. 2005, vol. 13, No. 5, p. 277-284.*
Chourasia et al., Drug Delivery, 2004, vol. 11, p. 129-148.*
El-Gibaly, I., International Journal of Pharmaceutics, 2002, vol. 232, p. 199-211.*
Chourasia et al., J Pharm Pharmaceut Sci, 2003, vol. 6, No. 1, p. 33-66.*
Cole et al., International Journal of Phrmaceutics, 2002, vol. 231, p. 83-95.*
Wommer et al., The Journal of Biological Chemistry, 2002, vol. 277, No. 27, p. 24142-24147.*
Arthur, M., et al., Heterogeneity of genes conferring high-level resistance to erythromycin by inactivation in enterobacteria(Abstract Only), Annales de L'Institut Pasteur, Microbiologie, Jan./Feb. 1986, pp. 125-134, vol. 137, No. 1.1.
Aydin Zuhal, et al., Preparation and evaluation of pectin beads, International Journal of Pharmaceutics, 1996, pp. 133-136, vol. 137.
Krishnaiah, Y. S. R., et al., Evaluation of guar gum as a compression coat for drug targeting to colon, International Journal of Pharmaceutics, 1998, pp. 137-146, vol. 171.
Milojevic, Snezana, et al., Amylose as a coating for drug delivery to the colon: preparation and in vitro evaluation using 5-aminosalicylic acid . . . , Journal of Controlled Release, 1996, pp. 75-84, vol. 38.
Munjeri, O., et al., Hydrogel beads based on amidated pectins for colon-specific drug delivery: the role of chitosan in modifying drug . . . , Journal of Controlled Release, 1997, pp. 273-278, vol. 46.
Munjeri, O., et al., An investigation into the suitability of amidated pectin hydrogel beads as a delivery matrix for chloroquine, Journal of Pharmaceutical Sciences, Aug. 1998, pp. 905-908, vol. 87, No. 8.
Noguchi, Norihisa, et al., Regulation of transcription of the mph(A) gene for macrolide 2'-phosphotransferase I in *Eschericha coli*: . . . , Journal of Bacteriology, Sep. 2000, pp. 5052-5058, vol. 182, No. 18.
Ounissi, Houria, et al., Nucleotide sequence of the gene ereA encoding the erythromycin esterase in *Escherichia coli* (Abstract Only), Gene, 1985, pp. 271-278, vol. 35, No. 3.

(Continued)

*Primary Examiner* — Kade Ariani
(74) *Attorney, Agent, or Firm* — Hultquist, PLLC; David Bradin

(57) ABSTRACT

Drug delivery systems for reducing the quantity of residual antibiotics reaching the colon following oral or parenteral antibiotic therapy, and for delivering metallo-dependent enzymes, and methods of use thereof, are disclosed. The drug delivery systems include pectin beads that encapsulate the active agent (which can be a metallo-dependent enzyme). The pectin is crosslinked with zinc or other divalent cations, and the pectin beads are coated with Eudragit®-type polymers. The delivery of the active agent can be modulated to occur at various pre-selected sites of delivery within the intestinal tract. A stable metallo-dependent enzyme formulation can be delivered to the lower intestine or colon. The use of zinc cations to crosslink the pectin is particularly preferred when the metallo-dependent enzymes are zinc dependent, where other cationic used to gel the pectin beads might adversely affect the activity of such metallo-dependent enzymes.

27 Claims, 7 Drawing Sheets

OTHER PUBLICATIONS

Rubinstein, Abraham, et al., Colonic drug delivery: enhanced release of indomethacin from cross-linked chondroitin matrix in rat cecal content, Pharmaceutical Research, 1992, pp. 276-278, vol. 9, No. 2.

Rubinstein, Abraham, et al., In vitro evaluation of calcium pectinate: a potential colon-specific drug delivery carrier, Pharmaceutical Research, 1993, pp. 258-263, vol. 10, No. 2.

Sriamornsak, Pornsak, Investigation of pectin as a carrier for oral delivery of proteins using calcium pectinate gel beads, International Journal of Pharmaceutics, 1998, pp. 213-220, vol. 169.

Sriamornsak, Pornsak, Effect of calcium concentration, hardening agent and drying condition on release characteristics of oral proteins . . . , European Journal of Pharmaceutical Sciences, 1999, pp. 221-227, vol. 8.

Wakerly, Z., et al., Pectin/ethylcellulose film coating formulations for colonic drug delivery, Pharmaceutical Research, 1996, pp. 1210-1212, vol. 13, No. 8.

* cited by examiner

Figure 2: Effect of Zinc % and PEI secondary coating on stability of beads containing β-Lactamase L1 in SIM

COLONIC DELIVERY OF METALLO-DEPENDENT ENZYMES

REFERENCE TO RELATED APPLICATION

This application claims priority to U.S. Ser. No. 60/859,599, filed on Nov. 17, 2006, the contents of which are hereby incorporated by reference.

FIELD OF THE INVENTION

The present invention is in the area of oral drug delivery systems to administer active agents to the colon. More specifically, the present invention relates to the delivery of metallo-dependent enzymes.

BACKGROUND OF THE INVENTION

Following their oral administration, antibiotics pass through the stomach and are then absorbed in the small intestine to diffuse in the whole organism and treat the infectious outbreak site(s) for which they have been administered. All the same, a fraction of antibiotics ingested (the importance of this fraction varies with the characteristics of each antibiotic) is not absorbed and continues its progress to the colon before being eliminated in the stool.

These residual antibiotics are combined, in the large intestine, with a fraction of the antibiotics absorbed, but which are re-excreted in the digestive tract by means of biliary elimination. This fraction is of variable importance as a function of metabolism and elimination pathways for each antibiotic. Finally, for certain antibiotics, a fraction of the dose absorbed is directly eliminated from the blood through the intestinal mucosa back into the lumen of the digestive tract, a good example is known with ciprofloxacin. Thus, whether administered orally or parenterally, a residual fraction of active antibiotics is generally found in the colon. This is the case, to varying degrees, for the great majority antibiotics from the various families used in therapeutics, with the sole notable exception of antibiotics from the amino-glycoside family for which intestinal excretion is negligible. For other antibiotics, intestinal excretion of a residual antibiotic activity will have a variety of consequences, all harmful. Indeed, the colon harbors a complex and very dense bacterial ecosystem (several hundreds of different bacterial species; more than $10^{11}$ bacteria per gram of colonic content) which will be affected by the arrival of active antibiotic residues. The following can be observed:

1. Flora imbalance which is the main cause of banal diarrhea occurring following antibiotic treatments (Bartlett J. G. (2002) Clinical practice. Antibiotic associated diarrhea, New England Journal of Medicine, 346, 334). Even though this diarrhea is generally not serious and ceases rapidly, either spontaneously, or upon completion of the antibiotic treatment, it is adversely perceived by patients and adds to the discomfort of the original illness for which the antibiotic was prescribed;

2. interference with the resistance to colonization by exogenic bacteria (or "barrier effect") with possible risk of infection, such as alimentary salmonella intoxication (Holmberg S. D. et al. (1984) Drug resistant Salmonella from animals fed antimicrobials, New England Journal of Medicine, 311, 617);

3. selection of microorganisms resistant to the antibiotic. These microorganisms can be of various types:
a) first they can be pathogenic bacteria such as for example, *Clostridium difficile*, a species capable of secreting toxins causing a form of colitis known as pseudomembranous colitis (Bartlett J. G. (1997) *Clostridium difficile* infection: pathophysiology and diagnosis, Seminar in Gastrointestinal Disease, 8, 12);

b) they can also be microorganisms that are relatively weakly pathogenic, but whose multiplication can lead to an associated infection (vaginal Candidosis or *Escherichia coli* resistant cystitis).

c) they can finally be non-pathogenic commensal drug-resistant bacteria whose multiplication and fecal elimination will increase dissemination of antibiotic resistance in the environment. It is well documented that antibiotic resistance genes are carried by mobile or transposable genetic elements that may contain up to 5 or 6 antibiotic resistance genes, and are readily transmitted to other bacteria, even across species. Consequently, these resistant commensal bacteria may constitute an important source leading to drug resistance for pathogenic species. This risk is currently considered seminal in terms of the disquieting character of the evolution towards drug multiresistance by numerous species pathogenic for humans.

It would be advantageous to provide drug delivery systems and methods for reducing the quantity of residual antibiotics reaching the colon following oral or parenteral antibiotic therapy. The present invention provides such drug delivery systems and methods.

SUMMARY OF THE INVENTION

Drug delivery systems for delivering metallo-dependent enzymes, and methods of treatment using the drug delivery systems, are disclosed. Also disclosed are drug delivery systems for delivering agents capable of reducing the quantity of residual antibiotics reaching the colon following oral or parenteral antibiotic therapy, and methods for using the drug delivery systems. In some embodiments, metallo-dependent enzymes are used to reduce the quantity of residual antibiotics reaching the colon. β-lactamase L1 from *Stenotrophomonas maltophilia* is one example of a metallo-dependent enzyme useful for reducing the quantity of residual antibiotics reaching the colon.

In other embodiments, one can use β-lactamases which are not metallo-enzymes (i.e., classes A, C or D). Moreover, one can use enzymes, metallo-dependent or otherwise, to inactivate other classes of antibiotics such as macrolides, quinolones and fluoriquinolones, glycopeptides, lipopeptides, cyclins, oxazolidinones, and other classes of antibiotics. The enzymes can have the full sequence of the native enzyme, or can be truncated or otherwise modified so long as they maintain acceptable activity.

The drug delivery systems include pectin beads crosslinked with zinc or any divalent cation of interest, which beads are then coated with Eudragit®-type polymers. When a metallo-dependent enzyme is encapsulated in the pectin bead, the cation used to crosslink the pectin comprises the same cation to which the enzyme is dependent.

The drug delivery systems are orally administrable, but can deliver the active agents to the colon. In some embodiments, they can administer the agents to various positions in the gastro-intestinal tract, including the colon.

Colon-specific delivery is obtained by formulating a metallo-dependent enzyme or an agent capable of reducing the quantity of residual antibiotics reaching the colon following oral or parenteral antibiotic therapy (which can be a metallo-dependent enzyme) with specific polymers that degrade in the colon, such as pectin. The pectin is gelled/crosslinked with a cation such as a zinc cation. The formulation, typically in the form of ionically crosslinked pectin beads, is subsequently coated with a specific polymer, such as a Eudragit® polymer.

The delivery can be modulated to occur at various preselected sites of delivery within the intestinal tract by gelling/crosslinking a mixture of the encapsulated agent, such as the metallo-dependent enzyme, and pectin, with divalent metallic cations such as $Ca^{2+}$ or $Zn^{2+}$.

Previous efforts have focused on coating pectin beads with cationic polymers such as polyethylene imine (PEI), chitosan or other cationic polymers, to prevent the pectin beads from degrading in the upper gastrointestinal tract. Such efforts are described, for example, in U.S. patent application Ser. No. 10/524,318, and U.S. Patent Application No. 60/651,352, the contents of which are hereby incorporated by reference.

The present invention relates to coating the pectin beads with Eudragit® polymers such as FS30D, L30D (also known as L30D-55), NE30D, mixtures thereof or other desirable types of Eudragit® to achieve the desired release of the encapsulated agent, such as β-lactamase L1, at predefined levels of the gastro-intestinal tract (GIT).

When the Eudragit® coating is dissolved, according to certain parameters such as pH or time, the beads are preferentially degraded by pectinolytic enzymes found in the lower part of the intestinal tract. Degradation of pectin then releases the agent encapsulated within the bead.

One aspect of the invention is to provide a stable metallo-enzyme formulation for the lower intestinal or colonic delivery of such an enzyme. The use of zinc cations to crosslink the pectin is particularly preferred when specific metallo-dependent enzymes, which are $Zn^{2+}$ dependent, could interact with other cationic species if they were used to gel the pectin beads. Such interactions could drastically affect the activity of such metallo-dependent enzymes. Accordingly, one embodiment of the drug delivery system involves using $Zn^{2+}$ ions as a crosslinking agent for the pectin beads and in association with $Zn^{2+}$ dependent enzymes which are very sensitive to the presence of other competitive cations. Of course, if the enzymes are dependent on other metal cations, such other metal cations (if they have a valence exceeding +1) can be used to crosslink the pectin.

The processes to obtain such beads can involve specific process conditions, such as time for gelification, washing, and drying that can be optimized to provide the highest quality beads, with optimized efficacy in vitro and in vivo. Therefore, another embodiment of the invention relates to processes for preparing zinc-crosslinked and Eudragit®-coated pectin beads.

DETAILED DESCRIPTION OF THE INVENTION

Figure 1:
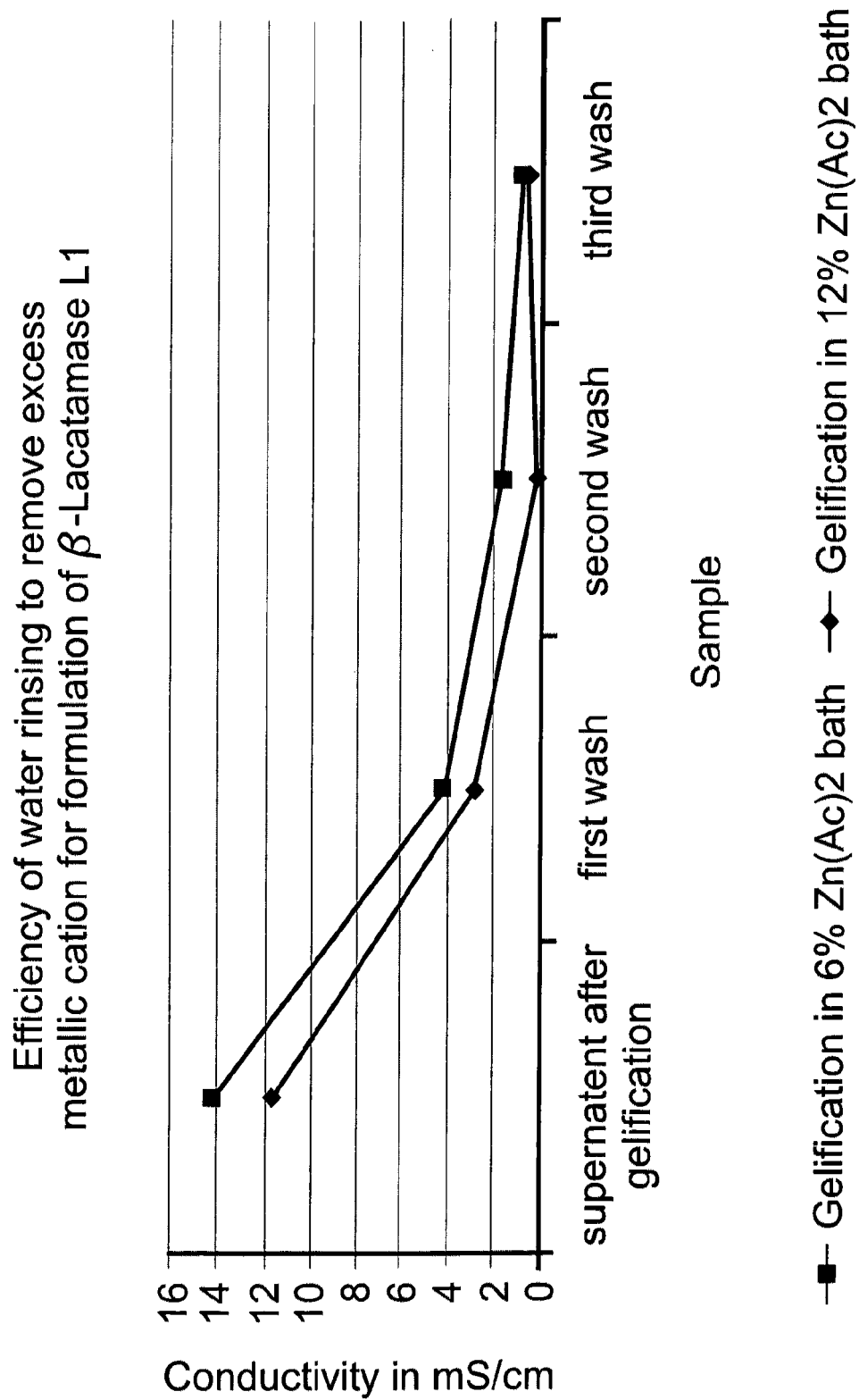
FIG. 1 is a graph showing the efficiency of water rinsing to remove excess metallic cations from a formulation of β-Lactamase L1 in pectin beads crosslinked with zinc acetate, measured in terms of conductivity (mS/cm) per sample following various washes.

The drug delivery systems described herein will be better understood with reference to the following detailed description.

I. Pectin Beads

The pectin beads are formed from pectin, zinc ions, and further coating with Eudragit® polymers and encapsulate one or more active agents.

Stability and protection of the pectin beads in gastric medium and intestinal medium is ensured by the Eudragit® polymer coating. In contrast, uncoated beads of pectin are not stable in such an environment and do not adequately protect their contents against degradation and/or inactivation. The Eudragit® coating ensures that they resist long enough so that their contents are able to reach the colon intact.

Pectin

Pectin is a polysaccharide isolated from the cellular walls of superior plants, used widely in the agricultural food industry (as a coagulant or thickener for jams, ice creams and the like) and pharmaceutics. It is polymolecular and polydisperse. Its drug delivery system varies depending on the source, extraction conditions and environmental factors.

Pectins are principally composed of linear chains of beta-1,4-D)-galacturonic acid, at times interspersed by units of rhamnose. The carboxylic groups of galacturonic acid can be partially esterified to yield methylated pectins. Two types of pectins are distinguished according to their degree of methylation (DM: number of methoxy groups per 100 units of galacturonic acid):

highly methylated pectin (HM: high methoxy) where the degree of methylation varies between 50 and 80%. It is slightly soluble in water and forms gels in acidic medium (pH<3.6) or in the presence of sugars;

weakly methylated pectin (LM: low methoxy), with a degree of methylation varying from 25 to 50%. More soluble in water than HM pectin, it gives gels in the presence of divalent cations such as $Ca^{2+}$ ions. Indeed, $Ca^{2+}$ ions form "bridges" between the free carboxylated groups of galacturonic acid moities. The network that is formed has been described by Grant et al. under the name of <<egg-box model>> (Grant G. T. et al. (1973) Biological interactions between polysaccharides and divalent cations: the egg-box model, FEBS Letters, 32, 195).

There are also amidated pectins. Treatment of pectin by ammonia transforms some methyl carboxylate groups (—COOCH$_3$) into carboxamide groups (—CONH$_2$). This amidation confers novel properties to the pectins, in particular better resistance to variations in pH. Amidated pectins tend to be more tolerant to the variations in pH, and have also been studied for the manufacture of matricial tablets for colonic delivery (Wakerly Z. et al. (1997) Studies on amidated pectins as potential carriers in colonic drug delivery, Journal of Pharmacy and Pharmacology. 49, 622).

Pectin is degraded by enzymes originating from higher plants and various microorganisms (fungi, bacteria, and the like) among which bacteria from the human colonic flora. The enzymes produced by the microflora encompass a mixture of polysaccharidases, glycosidases and esterases.

Metal Cations

Some metallo-dependent enzymes rely on zinc cations to function. Divalent zinc cations from various zinc salts can be used to crosslink pectin, as well as interact with the enzyme. Examples include zinc sulfate, zinc chloride, and zinc acetate.

Eudragit® Polymers

The coating of drug-loaded cores such as tablets, capsules, granules, pellets or crystals offers many advantages, such as higher physicochemical stability, better compliance and increased therapeutic efficiency of the active ingredients. Indeed, the. effectiveness of a medication depends not only on the actives it contains, but also on formulation and processing.

Poly(meth)acrylates have proven particularly suitable as coating materials. These polymers, of which only a few milligrams are employed, are pharmacologically inactive, i.e., are excreted unchanged.

EUDRAGIT® is the trade name for copolymers derived from esters of acrylic and methacrylic acid, whose properties are determined by functional groups. The individual EUDRAGIT® grades differ in their proportion of neutral, alkaline or acid groups and thus in terms of physicochemical properties. The skillful use and combination of different EUDRAGIT® polymers offers ideal solutions for controlled drug release in various pharmaceutical and technical applications. EUDRAGIT® provides functional films for sustained-release tablet and pellet coatings. The polymers are described in international pharmacopeias such as Ph. Eur., USP/NF, DMF and JPE.

EUDRAGIT® polymers can provide the following possibilities for controlled drug release:
  Gastrointestinal tract targeting (gastroresistance, release in the colon)
  Protective coatings (taste and odor masking, protection against moisture)
  Delayed drug release (sustained-release formulations).

EUDRAGIT® polymers are available in a wide range of different concentrations and physical forms (aqueous solution, aqueous dispersion, organic solution, solid substances).

The pharmaceutical properties of EUDRAGIT® polymers are determined by the chemical properties of their functional groups. A distinction is made between
  poly(meth)acrylates, soluble in digestive fluids (by salt formation)

EUDRAGIT® L, S, FS and E polymers with acidic or alkaline groups enable pH-dependent release of the active ingredient.

Applications: from simple taste masking via resistance solely to gastric fluid, to controlled drug release in all sections of the intestine
  poly(meth)acrylates, insoluble in digestive fluids EUDRAGIT® L and RS polymers with alkaline and EUDRAGIT® NE polymers with neutral groups enable controlled time release of the active by pH-independent swelling.

Enteric Coatings: Gastroresistance and Release in the Colon

Enteric EUDRAGIT® coatings provide protection against drug release in the stomach and enable controlled release in the intestine. Targeted drug release in the gastrointestinal tract is recommended for particular applications or therapeutic strategies, for example when the drug is sparingly soluble in the upper digestive tract, or when the drug may be degraded by gastric fluid. Secondly, this dosage form is very patient-friendly as it does not stress the stomach and the number of doses of the therapeutic drug can be considerably reduced, thanks to prolonged delivery. The dominant criterion for release is the pH-dependent dissolution of the coating, which takes place in a certain section of the intestine (pH 5 to over 7) rather than in the stomach (pH 1-5). For these applications, anionic EUDRAGIT® grades containing carboxyl groups, can be mixed with each other. This makes it possible to finely adjust the dissolution pH, and thus to define the drug release site in the intestine. EUDRAGIT® L and S grades are suitable for enteric coatings. EUDRAGIT® FS 30 D is specifically used for controlled release in the colon.

Application benefits of enteric EUDRAGIT® coatings include:
  pH-dependent drug release
  protection of actives sensitive to gastric fluid
  protection of the gastric mucosa from aggressive actives
  increase in drug effectiveness
  good storage stability
  controlled release in the colon/GI targeting Active Agents The active agent can be introduced into the drug delivery system as a powder, a solution, a suspension, or complexed with a solubilizing agent, such as a cyclodextrin or any other suitable compound.

Some of the active agents described herein can be administered in the form of prodrugs. Prodrugs have been widely studied for the colonic targeting of various active ingredients (such as steroid and non-steroid anti-inflammatory drugs, and spasmolytics). These systems are based on the capacity of the enzymes produced by the colonic flora to act on the prodrugs to release the active form of the active ingredient.

The prodrugs can be based on the action of bacterial azoreductases, so that the active agents are targeted to the colon with the drug delivery systems described herein, and the active agents are formed by reaction of the prodrug with a bacterial azoreductase, which provides a dual mechanism for ensuring that the drugs are administered to the colon. Representative chemistry for forming such prodrugs is described, for example, in Peppercorn M. A. et al. (1972) The role of intestinal bacteria in the metabolism of salicylazosulfapyridin, *The Journal of Pharmacology and Experimental Therapeutics,* 181, 555 and 64, 240.

Another approach consists in using bacterial hydrolases such as glycosidases and polysaccharidases (Friend D. R. (1995) Glycoside prodrugs: novel pharmacotherapy for colonic diseases, *S.T.P. Pharma Sciences,* 5, 70; Friend D. R. et al. (1984) A colon-specific drug-delivery system based on drug glycosides and the glycosidases of colonic bacteria, *Journal of Medicinal Chemistry,* 27, 261; Friend D. R et al. (1985) Drug glycosides: potential prodrugs for colon-specific drug delivery, *Journal of Medicinal Chemistry*, 28, 51; and Friend D. R. et al. (1992) Drug glycosides in oral colon-specific drug delivery, *Journal of Controlled Release*, 19, 109). Prodrugs have thus been developed by coupling, for example, sugar with steroids (glucose, galactose, cellobiose, dextrane (international application WO 90/09168)), cyclo-dextrins Hirayama F. et al. (1996) In vitro evaluation of Biphenylyl Acetic Acid-beta-Cyclodextrin conjugates as colon-targeting prodrugs: drug release behavior in rat biological media, *Journal of Pharmacy and Pharmacology*, 48, 27).

a) Agents that Inactivate Antibiotics

Any agent that inactivates an antibiotic can be administered. When the antibiotic is a beta-lactam antibiotic, β-lactamases can be used, and when the antibiotic is from another class of antibiotics, enzymes or other molecules that inactivate such antibiotics can be used. One such example would be to use an erythromycin esterase to inactivate macrolide antibiotics.

One representative enzyme is β-lactamase L1, a $Zn^{2+}$-dependent β-lactamase from *Stenotrophomonas maltophilia*, which was chosen from a series of β-lactamases because its characteristics showed the best profile for the targeted application. Also, it has demonstrated to have an excellent stability profile. The characteristics of various β-lactamases evaluated are described hereafter.

One representative erythromycin esterase is that disclosed by Andremont A. et al. ((1985) Plasmid mediated susceptibility to intestinal microbial antagonisms in *Escherichia coli Infect. Immun.* 49(3), 751), the contents of which are hereby incorporated by reference.

When the antibiotic is a quinolone, the active agent can be one capable of inactivating quinolones. Representative agents include those disclosed by Chen Y et al. ((1997) Microbicidal models of soil metabolisms biotransformations of danofloxacin *Journal of Industrial Microbiology and Biotechnology* 19, 378).

TABLE 1

| Antibiotics | FEZ-1 * $K_{cat}$ (s$^{-1}$) | $K_m$ (μM) | $K_{cat}/K_m$ (μM/s$^{-1}$) | L-1(wt) ** $K_{cat}$ (s$^{-1}$) | $K_m$ (μM) | $K_{cat}/K_m$ (μM/s$^{-1}$) |
|---|---|---|---|---|---|---|
| Penicillin | | | | | | |
| Benzylpenicillin | 70 | 590 | 0.11 | 600 | 38 | 16 |
| Ampicillin | >5.5 | >5000 | 0.011 | 520 | 55 | 9.5 |
| Cabenicillin | 35 | 1600 | 0.023 | | | |
| Pipericillin | 50 | 4200 | 0.012 | | | |
| Azlocillin | | | | | | |
| Mezlocillin | | | | | | |
| Ticarcillin | >65 | >5000 | 0.013 | | | |
| Timocillin | | | | | | |
| Cephalosporin | | | | | | |
| Cephaloridin | 16 | 1000 | 0.016 | | | |
| Cephalothin | 300 | 120 | 2.5 | 82 | 8.9 | 9.2 |
| Cefoxitin | | | | 1 | 3 | 0.33 |
| Cefuroxin | | | | | | |
| Cefotaxim | 165 | 70 | 2.4 | 270 | 10 | 27 |
| Ceftazidin | | | | | | |
| Cefepim | >6 | >1000 | 0.006 | | | |
| Cefpirom | | | | | | |
| Nitrocefin | 90 | 100 | 0.9 | 41 | 4 | 10 |
| Moxalactam | 3 | 18 | 0.17 | | | |
| Carbapenem | | | | | | |
| Imipenem | >200 | >1000 | 0.2 | 370 | 57 | 6.5 |
| Meropenem | 45 | 85 | 0.5 | 157 | 15 | 10 |
| Biapenem | 70 | >1000 | 0.07 | 134 | 32 | 4.2 |
| Monobactams | | | | | | |
| Aztreonam | | | | | | |
| Carumonam | | | | | | |
| Mechanism-Based Inactivators | | | | | | |
| Sulbactam | | | | | | |
| Tazobactam | 40 | 700 | 1.06 | | | |
| Clavulanic Acid | <0.01 | >1000 | <0.00001 | 11 | 22 | 0.5 |

| Antibiotics | IMP-1 *** $K_{cat}$ (s$^{-1}$) | $K_m$ (μM) | $K_{cat}/K_m$ (μM/s$^{-1}$) | VIM-2 **** $K_{cat}$ (s$^{-1}$) | $K_m$ (μM) | $K_{cat}/K_m$ (μM/s$^{-1}$) |
|---|---|---|---|---|---|---|
| Penicillin | | | | | | |
| Benzylpenicillin | 320 | 520 | 0.62 | 56 | 49 | 1.114 |
| Ampicillin | 950 | 200 | 4.8 | 125 | 90 | 1.4 |
| Cabenicillin | | | 0.02 | 185 | 205 | 0.9 |
| Pipericillin | | | 0.72 | 300 | 125 | 2.4 |
| Azlocillin | | | | 200 | 200 | 1 |
| Mezlocillin | | | | 200 | 125 | 1.4 |
| Ticarcillin | 1.1 | 740 | 0.0015 | 180 | 125 | 1.6 |
| Timocillin | | >2000 | <0.0001 | 7.7 | 390 | 0.002 |

TABLE 1-continued

Cephalosporin

| | | | | | | |
|---|---|---|---|---|---|---|
| Cephaloridin | 53 | 22 | 2.4 | 140 | 50 | 2.8 |
| Cephalothin | 48 | 21 | 2.4 | 130 | 11 | 12 |
| Cefoxitin | 16 | 8 | 2 | 15 | 13 | 1.2 |
| Cefuroxin | 8 | 37 | 0.22 | 8 | 20 | 0.4 |
| Cefotaxim | 1.3 | 4 | 0.45 | 70 | 12 | 5.8 |
| Ceftazidin | 8 | 44 | 0.18 | 3.6 | 72 | 0.05 |
| Cefepim | 7 | 11 | 0.66 | >40 | >400 | 0.1 |
| Cefpirom | 9 | 14 | 0.64 | 180 | 180 | 1 |
| Nitrocefin | 63 | 27 | 2.3 | 770 | 18 | 43 |
| Moxalactam | | | | 90 | 55 | 1.6 |

Carbapenem

| | | | | | | |
|---|---|---|---|---|---|---|
| Imipenem | 46 | 39 | 1.2 | 34 | 9 | 3.8 |
| Meropenem | 50 | 10 | | 5 | 2 | 2.5 |
| Biapenem | 160 | 28 | 6 | 8.5 | 15 | 0.55 |

Monobactams

| | | | | | | |
|---|---|---|---|---|---|---|
| Aztreonam | >0.01 | >1000 | <0.0001 | <0.01 | >1000 | <0.0001 |
| Carumonam | >0.01 | >1000 | <0.0001 | | | |

Mechanism-
Based
Inactivators

| | | | | | | |
|---|---|---|---|---|---|---|
| Sulbactam | | | | 23 | 320 | 0.072 |
| Tazobactam | | | | 28 | 875 | 0.032 |
| Clavulanic Acid | | | | | | |

\* (Mercuri et al., Antimicrob. Agents. Chemother. 2001 April; 45(4): 1254-1262)
\*\* (Carenbauer et al., BMC Biochem. 2002; 3: 4. Epub 2002 February 13; Frere, 2005, unpublished data)
\*\*\* (Murphy et al., 2003, Antimicrob. Ag. Chemother. 2003 February, 47(2): 582-7; Laraki et al., Antimicrob. Ag. Chemother. 1999 April, 43(4): 902-6)
\*\*\*\* (Docquier et al. J. Antimicrob. Chemother. 2003 February, 51(2): 257-266)

Patients can be treated with combinations of these agents.

b) Metallo-Dependent Enzymes

There are a variety of enzymes that are known to be metallo-dependent, in addition to the β-lactamase L1 enzyme discussed above. When it is desired to administer such enzymes to a patient via oral administration, care must be taken to avoid having the enzyme digested in the stomach or upper intestine. Accordingly, the drug delivery system described herein can advantageously be used to deliver such metallo-dependent enzymes. The cation used to crosslink the pectin comprises the cation on which the enzyme depends.

II. Methods for Preparing the Pectin Beads

Pectin beads can be prepared using methods known to those of skill in the art, including by mixing the active agent in a pectin solution, and gelification of the pectin anionic moieties by a divalent cation such as divalent zinc in the form of acetate solution for example.

This is typically done by stirring a solution, suspension or dispersion of the active agent, for example, β-lactamase L1, and pectin, adjusting the pH of the solution if necessary and adding this solution dropwise to a zinc acetate solution, or other solution comprising zinc ions, under agitation.

The technologies for adding the pectin solution dropwise to the zinc acetate solution are known to those of skill in the art; it includes the multi nozzle system from Nisco Engineering AG or any other relevant technology to produce drops from a pectin solution.

The pectin drops undergo a gelification process, ideally during a predetermined time to obtain the best encapsulation yield and subsequent release efficiency.

The concentration of the pectin solution is advantageously from 4 to 10% (w/v), preferably 4 to 7%, the zinc acetate solution is advantageously from 2 to 20% (w/v), preferably from 5 to 15%. More preferably, the pectin solution is about 5% (w/v), the zinc acetate solution is about 12% (w/v).

The pectin beads are advantageously stirred in the zinc acetate solution at a pH of about 6, at room temperature under slow agitation for at least 12 minutes up to 20 hours, preferably from 20 minutes to 2 hours.

The beads can then be recollected and rinsed in distilled water until conductivity of the rinsing solution reaches a plateau. Rinsing is preferably done at least twice or under a continuous process to minimize the amount of residual zinc acetate recovered in the rinsing solution.

The rinsed beads can then be collected and subjected to a drying process using methods known to those of skill in the art, including heated incubator or fluid bed technologies.

The beads are preferably dried at a temperature of between 20 and 40° C. for 30 min to 24 hours, preferably at 35° C. overnight. Drying is performed preferentially until the weight of the beads reaches a plateau.

The diameter of the particles can be finely tuned using needles of appropriate internal diameter to form the pectin drops added to the zinc acetate solution. The beads are preferably between about 600 and 1500 μm in diameter.

When the active agent is β-lactamase L1, the encapsulation yields are between 50 and 100%, measured in terms of enzymatic activity.

III. Formation of Drug Delivery Systems Including Pectin Beads

The pectin beads can be collected, and combined with appropriate excipients and formulated into a variety of oral drug delivery systems. For example, the beads can be combined with a solid excipient, and tableted, or included in a capsule.

The pectin beads can also be combined with liquid/gel excipients which do not degrade the pectin beads, and the mixture/dispersion can be incorporated into a capsule, such as a gel-cap.

The tablets or capsules can be coated, if desired, with a suitable enteric coating so as to assist in passing through the stomach without degradation. The pH in the stomach is of the order of 1 to 3 but it increases in the small intestine and the colon to attain values close to 7 (Hovgaard L. et al. (1996) Current Applications of Polysaccharides in Colon Targeting, *Critical Reviews in Therapeutic Drug Carrier Systems,* 13, 185). The drug delivery systems, in the form of tablets, gelatin capsules, spheroids and the like, can reach the colon, without being exposed to these variations in pH, by coating them with a pH-dependent polymer, insoluble in acidic pH but soluble in neutral or alkaline pH (Kinget et al., op. cit.). The polymers most currently used for this purpose are derivatives of methacrylic acid, Eudragit® L and S (Ashford M. et al. (1993), An in vivo investigation of the suitability of pH-dependent polymers for colonic targeting, *International Journal of Pharmaceutics,* 95, 193 and 95, 241; and David A. et al. (1997) Acrylic polymers for colon-specific drug delivery, *S.T.P. Pharma Sciences,* 7, 546), and, more recently, Eudragit® FS.

The drug delivery systems are administered in an effective amount suitable to provide the adequate degree of treatment or prevention of the disorders for which the compounds are administered. The efficient amounts of these compounds are typically below the threshold concentration required to elicit any appreciable side effects. The compounds can be administered in a therapeutic window in which some the disorders are treated and certain side effects are avoided. Ideally, the effective dose of the compounds described herein is sufficient to provide the desired effects in the colon but is insufficient (i.e., not at a high enough level) to provide undesirable side effects elsewhere in the body.

Most preferably, effective doses are at very low concentrations, where maximal effects are observed to occur, with minimal side effects, and this is optimized by targeted colonic delivery of the active agents. The foregoing effective doses typically represent that amount administered as a single dose, or as one or more doses administered over a 24-hour period.

IV. Methods of Treatment Using the Drug Delivery Systems Described Herein

The drug delivery systems described herein can be used to treat disorders which result from exposure of the colon to antibiotics, such as diarrhea, modification of the commensal flora, and the development of bacterial resistance to antibiotics, when the drug delivery systems contain agents which inactivate antibiotics. The active agents can be administered in a therapeutically effective dosage to a patient who has been, is being, or will be treated with one or several antibiotics.

When the metallo-dependent enzyme is an enzyme other than one which inactivates antibiotics, such enzyme can be administered to treat the specific disorders treated by such enzymes.

The present invention will be better understood with reference to the following non-limiting examples.

EXAMPLE 1

Development of a Sensitive, Quantitative and Specific Assay for β-lactamase L1

Hydrolysis of nitrocefin is a well known technique used to quantify penicillinase activity. However, the usual format is in single tubes and is not adapted for analysis of a large number of samples. This example describes the development and fit for purpose qualification of this assay in 96 wells microplate format Stock solution of Nitrocefin was obtained by solubilization of the Nitrocefin dried powder at a concentration of 10 mM in dimethylsulfoxide (DMSO). The stock solution was stored at −20° C. and diluted 100-fold immediately prior to use in 50 mM sodium phosphate buffer (Hepes buffer) pH 7.0 containing 0.1 mg/ml bovine serum albumin (BSA). Buffer selection is described in table I.

20 µl containing the solution to be analyzed were added to 180 µl of diluted Nitrocefin. Kinetics of Nitrocefin hydrolysis are followed at 37° C. with a measure of absorbance at 492 nm each 30 seconds using a Multiskan Ascent (Thermo Labsystems) plate reader.

The slope (difference in absorbance/second) was calculated using Excel Adds In Cellular (Prism Technologies, Cambridge UK).

β-lactamase L1 (Eurocent, Belgium, approx. 10 mg/mol as determined by µBCA assay) was diluted 500×, 1000×, 2000× and 4000× in each solubilization buffer and reaction was initiated by addition of 20 µl of solution containing enzyme to 180 µl of buffers containing nitrocefin at 100 µM.

Activity of β-lactamase L1 was tested in 10 mM Hepes, 145 mM NaCl buffer pH 7.4. The interference of EDTA with the activity of the metallo-dependent enzyme and need for carrier protein (Bovine Serum Albumin abbreviated as BSA) were tested. As illustrated in Table 1, EDTA (that can be used to solubilize beads in vitro to assay their contents) should be avoided. The inclusion of BSA or another carrier protein is beneficial.

TABLE 1

Selection of buffer drug delivery system for β-lactamase L1 activity quantification

| Buffer | Slope | Yield |
|---|---|---|
| 10 mM Hepes, 145 mM NaCl pH 7.4 | 0.142 | 100% |
| 10 mM Hepes, 145 mM NaCl, 1% EDTA pH 7.4 | 0.026 | 18.8% |
| 10 mM Hepes, 145 mM NaCl, 0.1 mg/ml BSA pH 7.4 | 0.167 | 118.2% |
| 10 mM Hepes, 145 mM NaCl, 0.1 mg/ml BSA, 1% EDTA pH 7.4 | 0.084 | 59.0% |

As illustrated in Table 1, EDTA interferes in enzymatic activity assay, whereas BSA enhances the recovery of enzymatic activity.

EXAMPLE 2

Instability of β-lactamase L1 In Original Pectin Mix and Effect of Metallic Counter-Ion 0.3 ml of β-lactamase L1 (Eurogentec, Belgium, approx. 10 mg/mL as determined by µBCA assay) was mixed to 10 g of a 6% pectin solution (Low methoxylated amidated pectin (Unipectine), Texturant Systems, cat# OG175C) made in water; the pH of the pectin solution was not adjusted.

The pectin/β-lactamase L1 mixture was added drop-wise over a period of 2 minutes using a peristaltic pump and a needle of 0.8 mm inner diameter to a beaker containing 40 ml of calcium chloride (6%) under agitation (200 rpm) at room temperature.

After further incubation to allow equilibration between free and bound calcium ions, beads were recovered by filtration and washed 3 times in 200 ml of purified water to eliminate excess of free calcium. At this stage, beads are referred to as "gelled beads".

Beads were dried 2 hours at 37° C. in an oven, yielding dried beads.

2×5 droplets and 2×15 droplets were sampled at the exit of the needle to measure the initial β-lactamase L1 activity. Protein-free beads were also prepared as negative controls.

The β-lactamase L1 enzymatic activity (nitrocefin hydrolysis) was quantified with and without Zn ions (0.1 mM $ZnCl_2$) as described in Example 1.

As illustrated in Table 2, no enzymatic activity was found in the β-lactamase L1/pectin mix while significant activity was recovered in the beads assayed in buffer containing Zn.

TABLE 2

Inactivation of β-lactamase L1 in non pH-adjusted pectin solution

| Slope/min | Without ZnAc | With ZnAc |
|---|---|---|
| Before mix with pectin | 0.105 (100.0%) | 0.103 (100.0%) |
| β-Lactamase/pectin mix | 0.000 (0.0%) | 0.000 (0.0%) |
| Gelled milli particles | 0.0078 (7.4%) | 0.042 (40.7%) |

EXAMPLE 3

Optimization of Metallic Ion Used to Gel the Pectin, and the Effect of pH of the Pectin Solution.

In order to decipher the effects of the pectin solution parameters and Zinc ions, an experiment comparing four formulations was performed (design was build according to factorial design, Design Expert 6.0.10, Stat-Ease, Mineapollis). Two parameters were tested:
(a) pH of the pectin solution: 4.0 and 7.0
(b) metallic cation in the gelification bath: $Ca^{2+}$ ($CaCl_2$) or $Zn^{2+}$ (Zinc acetate abbreviated ZnAc)

Beads were prepared as described in Example 2. However, the concentration of the pectin solution was decreased from 6% to 4% due to the decrease in solubility of pectin with increased pH. The encapsulation yield was measured by assaying the enzymatic activity of β-Lactamase L1 as described in Example 1.

5 beads were solubilized in 20 ml of 10 mM Hepes, 145 mM NaCl, 0.1 mg/ml BSA pH 7.4 in the presence or absence 1% pectinase (Pectinases from Aspergillus Aculeatus, Pectinex SP-L Ultra, SIGMA, France) overnight at 4° C.

The positive control consisted in diluting the same amount of β-lactamase L1 as should be contained in 5 beads in 20 ml of 10 mM Hepes, 145 mM NaCl, 0.1 mg/ml BSA pH 7.4.

As illustrated in Table 3, β-lactamase L1 is inactivated irrespective of the cation used for pectin gelification when the pectin solution is at pH 4.0 (4.3% residual activity in Calcium and 3.8% in Zinc), whereas nearly full activity is retained after buffering the pectin solution to pH 7.0 (86.7% in Calcium and 64.0% in Zinc).

TABLE 3

Effect of cation used for gelification and pH of pectin on stability (recovery of β-Lactamase activity)

| Sample | $CaCl_2$ pH 4 | $CaCl_2$ pH 7 | ZnAc pH 4 | ZnAc pH 7 |
|---|---|---|---|---|
| Before mix | 0.102 (100%) | 0.090 (100%) | 0.108 (100%) | 0.090 (100%) |
| Gelled beads | 0.004 (4.3%) | 0.072 (80.0%) | 0.004 (3.8%) | 0.072 (80.0%) |
| Dried beads | 0.003 (31.7%) | 0.078 (86.7%) | 0.037 (35.0%) | 0.058 (64.0%) |

EXAMPLE 4

Determination of Critical Parameters to Formulate β-Lactamase L1 for Colon-Specific Delivery and Optimization of These Parameters Five parameters were tested:
(a) Concentration of the pectin solution (Low methoxylated amidated pectin (Unipectine), Texturant Systems, cat# OG175C): 4% and 5% (w/v)
(b) Cation for gelification: $Ca^{2+}$ or $Zn^{2+}$
(c) Secondary coating of the gelled beads with polyethyleneimine (PEI) solution (PEI, High molecular weight, water-free, SIGMA-ALDRICH, France)
(d) pH of the PEI solution: 7 and 11 (original non ph-adjusted solution).
(e) Solubilization of the beads to assay the encapsulated enzymatic activity with and without 1% pectinase Table 4 summarizes the experimental design

TABLE 4

Experimental design for the optimization of critical parameters involved in β-Lactamase L1 formulation

| Run | A: Pectin (%) | B: Ion | C: PEI Coating | D: pH of PEI | E: Pectinase |
|---|---|---|---|---|---|
| 1 | 5 | $Zn^{2+}$ | Yes | 11 | Yes |
| 2 | 4 | $Zn^{2+}$ | Yes | 7 | Yes |
| 3 | 5 | $Ca^{2+}$ | No | | Yes |
| 4 | 4 | $Ca^{2+}$ | Yes | 7 | No |
| 5 | 5 | $Ca^{2+}$ | Yes | 7 | Yes |
| 6 | 4 | $Ca^{2+}$ | No | | Yes |
| 7 | 4 | $Zn^{2+}$ | Yes | 11 | No |
| 8 | 5 | $Ca^{2+}$ | Yes | 11 | No |
| 9 | 4 | $Ca^{2+}$ | Yes | 11 | Yes |
| 10 | 4 | $Zn^{2+}$ | No | | No |
| 11 | 5 | $Zn^{2+}$ | No | | Yes |
| 12 | 4 | $Zn^{2+}$ | No | | Yes |
| 13 | 5 | $Zn^{2+}$ | Yes | 7 | No |
| 14 | 5 | $Ca^{2+}$ | No | | No |
| 15 | 4 | $Ca^{2+}$ | No | | No |
| 16 | 5 | $Zn^{2+}$ | No | | No |

These 16 experiments were performed in duplicate (32 results), and run 13 was replicated (34 results). The pH of the 4% and 5% pectin solutions was adjusted to 7.0. However, it was discovered that the pH of the 5% pectin solution was unstable and decreased to pH 5.4 by the end of the experiments. A 5% pectin solution was therefore also adjusted to pH 8.5 for comparison. Finally, the 48 results were analyzed using Factorial Design.

Beads were prepared as described in Example 2 except that the gelification time in the cation bath was reduced from 20 min to 10 min to allow a smart timing of the experiments.

Samples (5 beads) were solubilized overnight at 4° C. in 20 ml of 10 mM Hepes, 145 mM NaCl, 0.1 mg/ml BSA pH 7.4 with and without 1% pectinase before measuring enzymatic activity (nitrocefin hydrolysis as described in Example 1).

Tale 5 summarizes the experimental results obtained.

TABLE 5

Full results of Experimental design for optimizing critical parameters involved in β-Lactamase L1 formulation

| Run | % pectin | pH pectin | ion | PEI | pH of PEI | pectinase | yield |
|---|---|---|---|---|---|---|---|
| 1 | 5 | 5.4 | $Zn^{2+}$ | yes | 11 | yes | 1.201 |
| 17 | 5 | 5.4 | $Zn^{2+}$ | yes | 11 | yes | 1.13 |
| 3b | 5 | 5.4 | $Zn^{2+}$ | yes | 11 | yes | 1.39 |
| 11 | 5 | 5.4 | $Zn^{2+}$ | no | | yes | 1.272 |
| 27 | 5 | 5.4 | $Zn^{2+}$ | no | | yes | 1.36 |
| 2b | 5 | 5.4 | $Zn^{2+}$ | no | | yes | 1.044 |
| 1b | 5 | 5.4 | $Zn^{2+}$ | yes | 7 | yes | 1.045 |
| 13 | 5 | 5.4 | $Zn^{2+}$ | yes | 7 | no | 0.687 |
| 29 | 5 | 5.4 | $Zn^{2+}$ | yes | 7 | no | 0.72 |
| 33 | 5 | 5.4 | $Zn^{2+}$ | yes | 7 | no | 0.661 |
| 34 | 5 | 5.4 | $Zn^{2+}$ | yes | 7 | no | 0.691 |
| 16 | 5 | 5.4 | $Zn^{2+}$ | no | | no | 0.762 |
| 32 | 5 | 5.4 | $Zn^{2+}$ | no | | no | 0.788 |
| 45 | 5 | 8.5 | $Zn^{2+}$ | no | | yes | 0.951 |
| 38 | 5 | 8.5 | $Zn^{2+}$ | no | | yes | 0.818 |
| 41 | 5 | 8.5 | $Zn^{2+}$ | no | | no | 0.245 |
| 48 | 5 | 8.5 | $Zn^{2+}$ | no | | no | 0.363 |
| 46 | 5 | 8.5 | $Zn^{2+}$ | yes | 7 | no | 0.815 |
| 39 | 5 | 8.5 | $Zn^{2+}$ | yes | 7 | no | 0.826 |
| 2 | 4 | 7 | $Zn^{2+}$ | yes | 7 | yes | 1.01 |
| 18 | 4 | 7 | $Zn^{2+}$ | yes | 7 | yes | 1.162 |
| 12 | 4 | 7 | $Zn^{2+}$ | no | | yes | 1.165 |
| 28 | 4 | 7 | $Zn^{2+}$ | no | | yes | 1.148 |
| 7 | 4 | 7 | $Zn^{2+}$ | yes | 11 | no | 0.727 |
| 23 | 4 | 7 | $Zn^{2+}$ | yes | 11 | no | 0.679 |
| 10 | 4 | 7 | $Zn^{2+}$ | no | | no | 0.674 |
| 26 | 4 | 7 | $Zn^{2+}$ | no | | no | 0.659 |
| 3 | 5 | 5.4 | $Ca^{2+}$ | yes | 7 | yes | 0.094 |
| 5 | 5 | 5.4 | $Ca^{2+}$ | yes | 7 | yes | 0.031 |
| 19 | 5 | 5.4 | $Ca^{2+}$ | yes | 7 | yes | 0.108 |
| 21 | 5 | 5.4 | $Ca^{2+}$ | yes | 7 | yes | 0.039 |
| 8 | 5 | 5.4 | $Ca^{2+}$ | yes | 11 | no | 0.047 |
| 24 | 5 | 5.4 | $Ca^{2+}$ | yes | 11 | no | 0.066 |
| 14 | 5 | 5.4 | $Ca^{2+}$ | no | | no | 0.488 |
| 30 | 5 | 5.4 | $Ca^{2+}$ | no | | no | 0.512 |
| 35 | 5 | 8.5 | $Ca^{2+}$ | yes | 7 | yes | 0.35 |
| 36 | 5 | 8.5 | $Ca^{2+}$ | yes | 7 | yes | 0.379 |
| 42 | 5 | 8.5 | $Ca^{2+}$ | yes | 7 | yes | 0.363 |
| 43 | 5 | 8.5 | $Ca^{2+}$ | yes | 7 | yes | 0.394 |
| 4b | 5 | 8.5 | $Ca^{2+}$ | yes | 7 | yes | 0.53 |
| 7b | 5 | 8.5 | $Ca^{2+}$ | yes | 7 | no | 0.704 |
| 37 | 5 | 8.5 | $Ca^{2+}$ | yes | 11 | no | 0.029 |
| 44 | 5 | 8.5 | $Ca^{2+}$ | yes | 11 | no | 0.029 |
| 9b | 5 | 8.5 | $Ca^{2+}$ | yes | 11 | no | 0.737 |
| 40 | 5 | 8.5 | $Ca^{2+}$ | | | no | 0.322 |
| 47 | 5 | 8.5 | $Ca^{2+}$ | | | no | 0.656 |
| 6b | 5 | 8.5 | $Ca^{2+}$ | yes | 11 | yes | 0.517 |
| 5b | 5 | 8.5 | $Ca^{2+}$ | no | | yes | 0.656 |
| 8b | 5 | 8.5 | $Ca^{2+}$ | no | | no | 0.967 |

Simple mono-variate statistical analysis (decreasing yield of encapsulation sorting) highlighted that optimal formulation of β-lactamase L1 was obtained using the following parameters (a) A pectin concentration of 5% (maximum solubility at pH 5.4)

(b) The pectin solution should be neutralized to a pH of at least 5.4

(c) Zinc ion should be used (e) Pectinase should be used to quantify the enzymatic activity of encapsulated β-lactamase L1.

EXAMPLE 5

Improvement of Stability of the Beads Comprising β-Lactamase L1 in Simulated Intestinal Media (SIM) by Increased Zinc Ion Concentration and Duration of Drying Beads containing β-lactamase L1 were prepared as described in Example 4. Increasing Zinc acetate concentrations (6, 8, 10 and 12%) were tested. Further coating with or without PEI were compared. The time for drying the beads was also increased from 2 hours to overnight. The efficiency of washing the beads to remove excess metallic ion used for gelification was also monitored by measuring the conductivity of the water rinsing solution. As illustrated in FIG. 1, efficient washing was obtained after 3 water washes of the beads.

As illustrated in Table 6, the higher concentration of zinc ions increased stability in SIM (Simulated Intestinal Medium, US Pharmacopeia 26) of the beads containing β-lactamase L1, while a PEI secondary coating decreased their stability.

TABLE 6

Effect of Zinc acetate concentration and PEI secondary coating on stability of beads containing β-Lactamase L1 in SIM

| | | | SIM | | | | |
|---|---|---|---|---|---|---|---|
| Run# | % Zn | PEI | 1 h | 2 h | 3 h | 4 h | 5 h |
| 8 | 10% | N | + | + | + | + | + |
| 3 | 12% | Y | + | + | + | + | + |
| 4 | 12% | N | + | + | + | + | + |
| 2 | 8% | N | + | + | + | + | + |
| 5 | 6% | Y | − | − | − | − | − |
| 1 | 8% | Y | + | + | − | − | − |
| 7 | 10% | Y | + | − | − | − | − |

+: stable beads
−: dissolved beads
Y: with PEI secondary coating
N: without PEI secondary coating

EXAMPLE 6

Effect of Zinc Concentration and Drying Time on the Stability of Beads in Simulated Intestinal Media (SIM)

Beads containing β-lactamase L1 were prepared as previously described, and gelled with 6 or 12% zinc acetate solutions (see Example 5). The effect of drying time was also tested by drying beads for 2, 4 and 16 h at 35° C. (temperature preferred to 37° C. for industrialization purposes). Only beads gelled in the 12% zinc solution and dried for more than 4 h were stable in SIM after 5 h incubation at 37° C.

TABLE 7

Stability of beads in Simulated Intestinal Medium for 5 h at 37° C.

| | Incubation at 37° C. (h) | 2 h drying | 4 h drying | Overnight |
|---|---|---|---|---|
| milli-particles in 6% Zn | 1 | 5 | 0 | 0 |
| | 2 | 1 | 0 | 0 |
| | 3 | 1 | 0 | 0 |
| | 4 | 1 | 0 | 0 |
| | 5 | 1 | 0 | 0 |

TABLE 7-continued

Stability of beads in Simulated Intestinal Medium for 5 h at 37° C.

| | Incubation at 37° C. (h) | 2 h drying | 4 h drying | Overnight |
|---|---|---|---|---|
| milli-particles in 12% Zn | 1 | 5 | 5 | 5 |
| | 2 | 5 | 5 | 5 |
| | 3 | 5 | 5 | 5 |
| | 4 | 4 | 5 | 5 |
| | 5 | 3 | 4 | 5 |

The numbers represent the number of beads still apparently intact in solution. After washing and further incubation in Simulated Colonic Medium (SCM: 10 mM Hepes, 145 mM NaCl (stock solution). 1% pectinase, 0.1 mg/ml BSA were added just before use; pH was adjusted to pH 6.0 with NaOH 1 M), 63% of the initial β-lactamase activity (nitrocefin hydrolysis) was recovered.

EXAMPLE 7

Effect of Gelification Time, Rinsing Process, and Drying Time on Recovery of β-Lactamase L1 Activity Different batches of beads were prepared using a multi-nozzle system from Nisco Engineering AG. The beads underwent various gelification times, rinsing process and time and drying process type and time.

Figure 2:
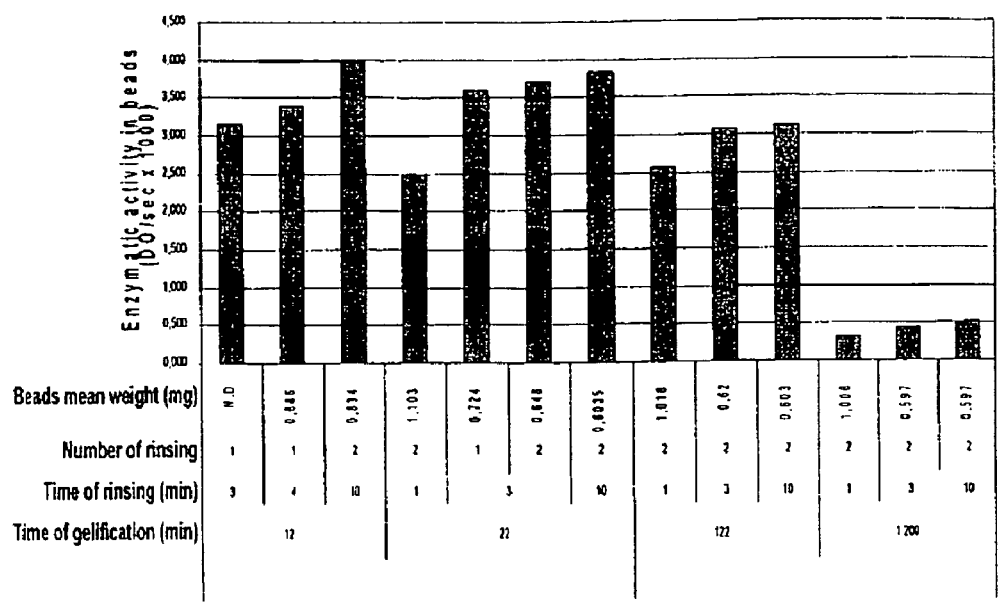
FIG. 2 is a graph showing the effect of gelification time, rinsing process, and drying time on recovery of β-Lactamase L1 activity.
Figure 3:
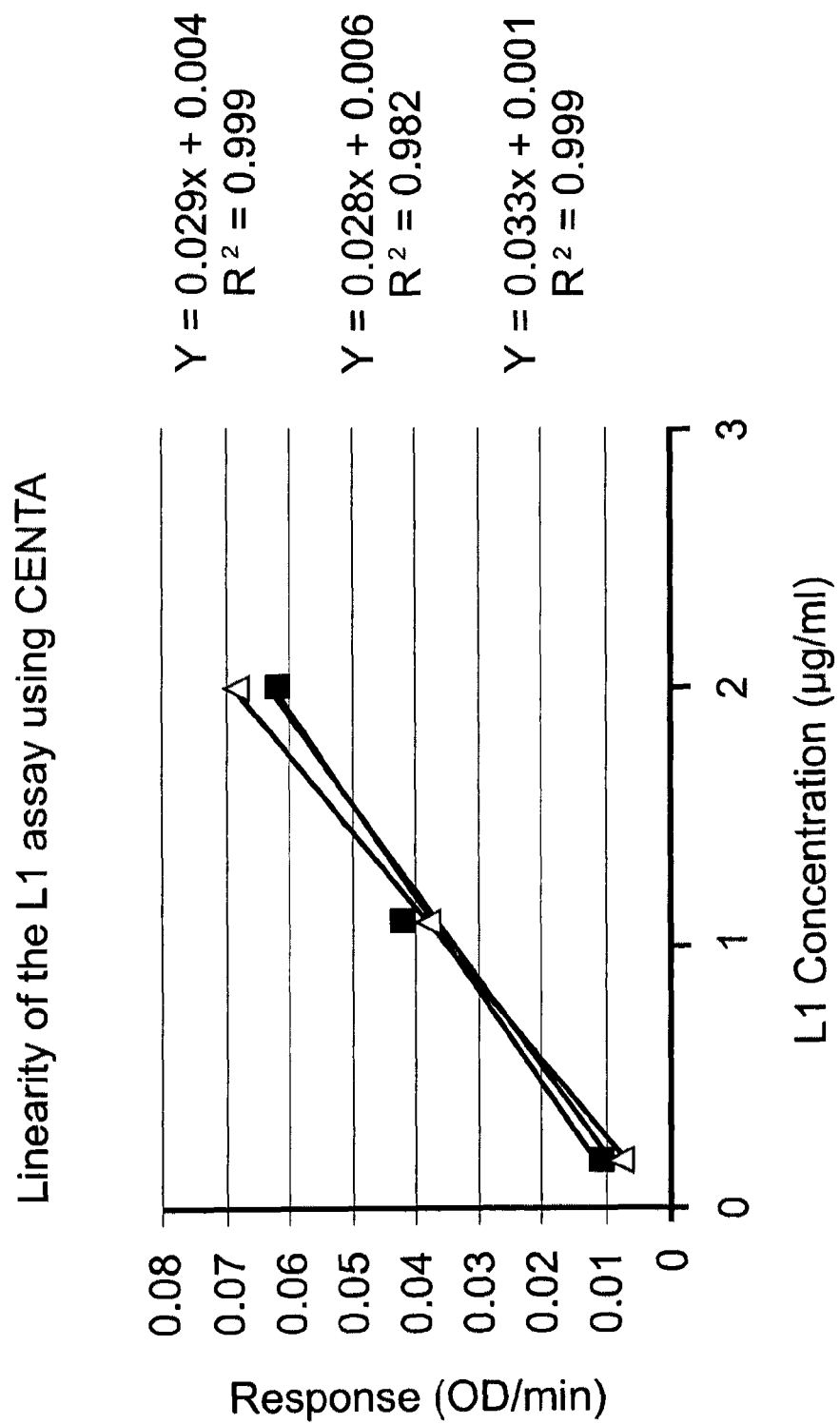
FIG. 3 is a graph showing the enzymatic activity of β-lactamase L1 using CENTA as a substrate, measured in terms of response (OD/min) versus L1 concentration (μg/ml).

It appears clearly that the best encapsulation efficiency and enzyme activity are obtained when gelification time is less than 20 hours and when rinsing is performed such as to eliminate residual Zinc acetate from the beads. The results are presented in FIG. 2.

EXAMPLE 8

Development of a Sensitive, Quantitative and Specific Assay for β-lactamase L1

Hydrolysis of CENTA is a well known technique used to quantify β-lactamase activity. However, the usual format is in single tubes and is not adapted for analysis of a large number of samples. This example describes the development and fit for purpose qualification of this assay in 96 wells microplate format A stock solution of CENTA was obtained by solubilization of the CENTA dried powder at a concentration of 25 mM in water; it was stored in 25 μl aliquots at −20° C. The assay mix was done by diluting 22 μl of CENTA stock solution in the following assay buffer: 10 ml 30 mM Hepes buffer pH 7.5 containing 50 μm $ZnCl_2$, hence yielding a CENTA concentration of 110 μM. For the assay, 20 μl containing the enzyme to be assayed were added to 180 μl of assay mix, hence using a final concentration of 100 μM CENTA In the assay. Kinetics of CENTA hydrolysis were followed at 37° C. with a measure of absorbance at 405 nm each 9 seconds using a Multiskan Ascent (Thermo Electron Corporation) plate reader. The slope (difference in absorbance/second) was calculated using Ascent Software for Multiskan Ascent version 2.6.

β-lactamase L1 (Eurogentec, Belgium, approx. 10 mg/mL as determined by μBCA assay) was diluted to 0.2, 0.5, 1.0 and 2.0 μg/ml in assay buffer and the reaction was initiated by addition of 20 μl of enzyme-containing solution to 180 μl of assay mix. As shown in Figure below, the assay was linear in 3 independent assays with respect to enzyme concentration in that range. Standard deviation was less than 10%.

EXAMPLE 9

Release of β-lactamase L1 from Uncoated Beads, and Eudragit-coated Beads with or without HPMC Pre-coating A batch of pectin beads containing β-lactamase L1 was manufactured under the following conditions: beads were formed by adding dropwise through a 0.5 mm internal diameter needle a solution of 5% pectin containing 300 mg/l purified recombinant β-lactamase L1 (Eurogentec, Belgium) to a 12% bath of Zn acetate, $2H_2O$. Beads were gelified for 90 min in the Zn acetate bath, collected, washed with water untill the water conductivity had reached a stable plateau, signifying that rinsing is optimal and finally dried at 35° C. under vacuum. Dried beads obtained were 0.8-1.25 mm diameter, weighed on average 0.6 mg and contain approx 5 to 6 μg β-lactamase L1 per mg of beads. They were either left uncoated, or coated using a Glatt GPC 1.1 with Top spray according to the following formulas shown in Table 9.

TABLE 9

| Raw materials | Amount (g) Batch 83 | Amount (g) Batch 100 | Amount (g) Batch 82 | Amount (g) Batch 99 | Amount (g) Batch 81 | Amount (g) Batch 97 |
|---|---|---|---|---|---|---|
| Eudragit L30D-55 | 1600.0 | 149.5 | 300.0 | 31.9 | | |
| Eudragit NE 30 D | | | 700.0 | 74.4 | | |
| Eudragit FS30D | | | | | 800.0 | 85.0 |
| GMS (Glycerol monostearate) | 24.0 | 2.2 | 15.0 | 1.6 | 12.0 | 1.3 |
| Sodium Hydroxide | 28.8 | 2.7 | 30.4 | 1.9 | | 1.5 |
| Tween 80 (polysorbate) 33% Aqueous solution | 48.0 | 2.2 | 18.0 | 1.6 | 14.4 | 1.3 |
| Triethyl Citrate | 1107.2 | 94.5 | 4.50 | 67.2 | 10.0 | 25.2 |
| Water | 1600.0 | 149.5 | 565.7 | 1600.0 | 505.6 | 85.0 |
| Pre-coating with 5% HPMC | NO | YES | NO | YES | NO | YES |

Pre-coating of beads was performed with HPMC using same material as for the coating with Eudragit.

Figure 4:
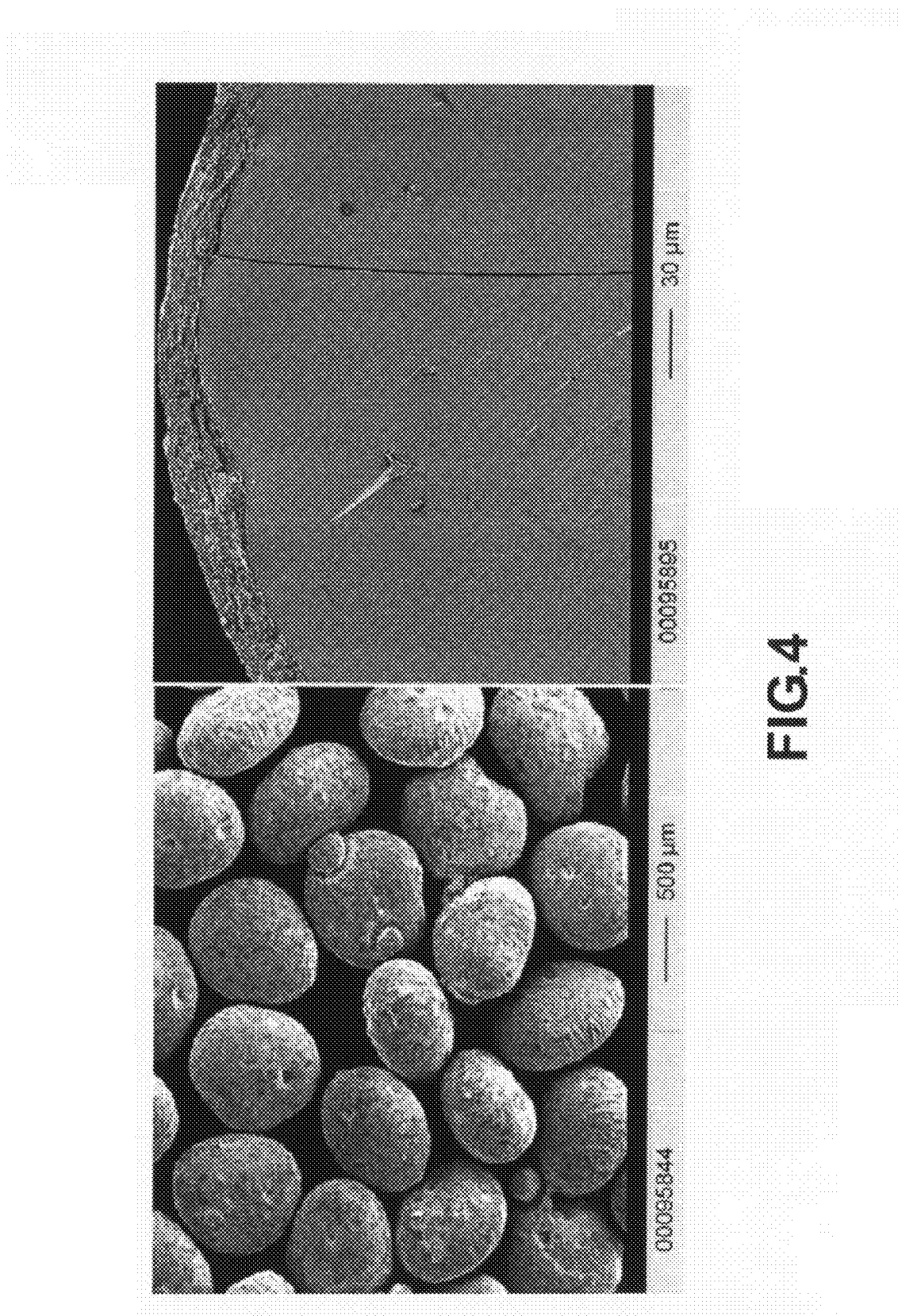
FIG. 4 is a series of scanning electron micrographs showing Eudragit-coated beads prepared using the methods described herein, and a cross-section of the beads showing the approximate thickness of Eudragit layer.

Scanning electron micrographs (SEMs) of Eudragit-coated beads are shown in FIG. 4. A cross-section shows the relative thickness of the Eudragit coating.

In order to assess the release of β-lactamase L1, coated and uncoated beads were incubated under gentle mixing at 37° C. in 50 mM Hepes buffer pH 7.4 containing 0.1 M NaCl and 100 PG/ml pectinases from *Aspergillus aculeatus* (Sigma Aldrich). Medium was withdrawn at various times and assayed for β-lactamase activity using the nitrocephin assay described in Example 1.

Figure 5:
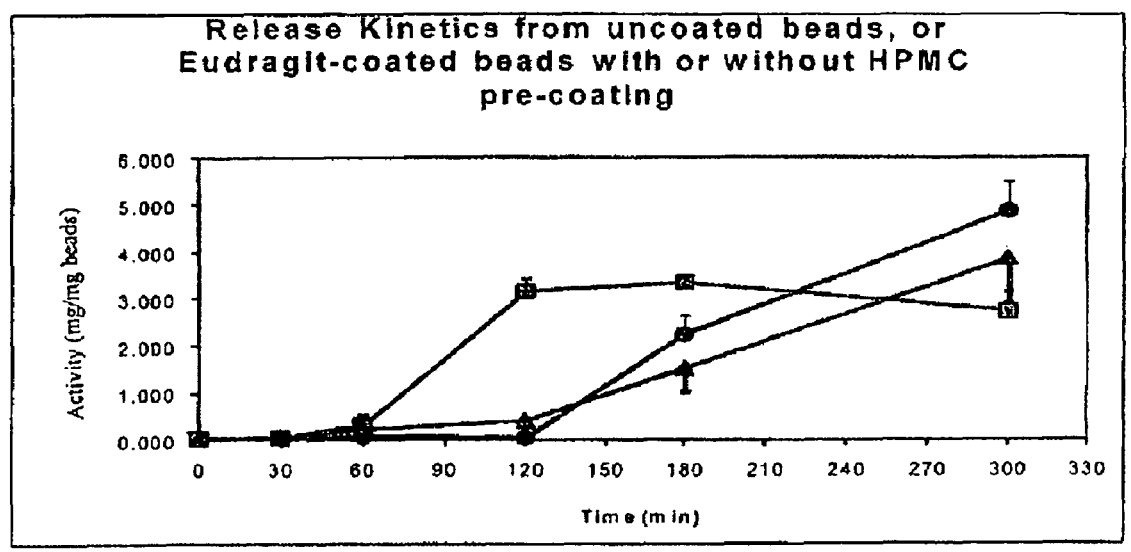
FIG. 5 is a chart showing the release kinetics of β-lactamase L1 from uncoated beads, and Eudragit-coated beads with or without hydroxypropyl methyl cellulose (HPMC) pre-coating, measured in terms of activity (μg/mg beads) versus time (minutes). Blue triangles represent uncoated beads; red circles represent beads coated with 40% Eudragit L30D-55 without pre-coating; green squares represent beads pre-coated with 5% HPMC and coated with 40% Eudragit L30D-55.

Release kinetics were measured using the coated and uncoated beads, and the results are shown in FIG. 5.

EXAMPLE 10

Efficiency of Released L1 to Hydrolyze Antibiotics in vitro

In order to assess whether coated beads would actually be able to hydrolyze antibiotics when they reach the colon, they were successively incubated for 1 h in simulated gastric medium (0.1N HCl), 3 h at 37° C. in simulated intestinal medium (50 mM Na/K phosphate buffer pH 6.8 containing 0.1 M NaCl) and finally for the indicated amounts of time in simulated colonic medium (50 mM Hepes buffer pH 7.4, 0.1 M NaCl) containing 100 PG/ml pectinases from *Aspergillus aculeatus* (Sigma Aldrich) and 2 mg/ml amoxicillin. Medium was withdrawn at various times and the amount of residual amoxicillin was measure by HPLC and UV absorption. The procedure was performed using a Bio-Diss III apparatus (Varian). Uncoated beads were only incubated in the simulated colonic medium with pectinases and amoxicillin.

Figure 6:
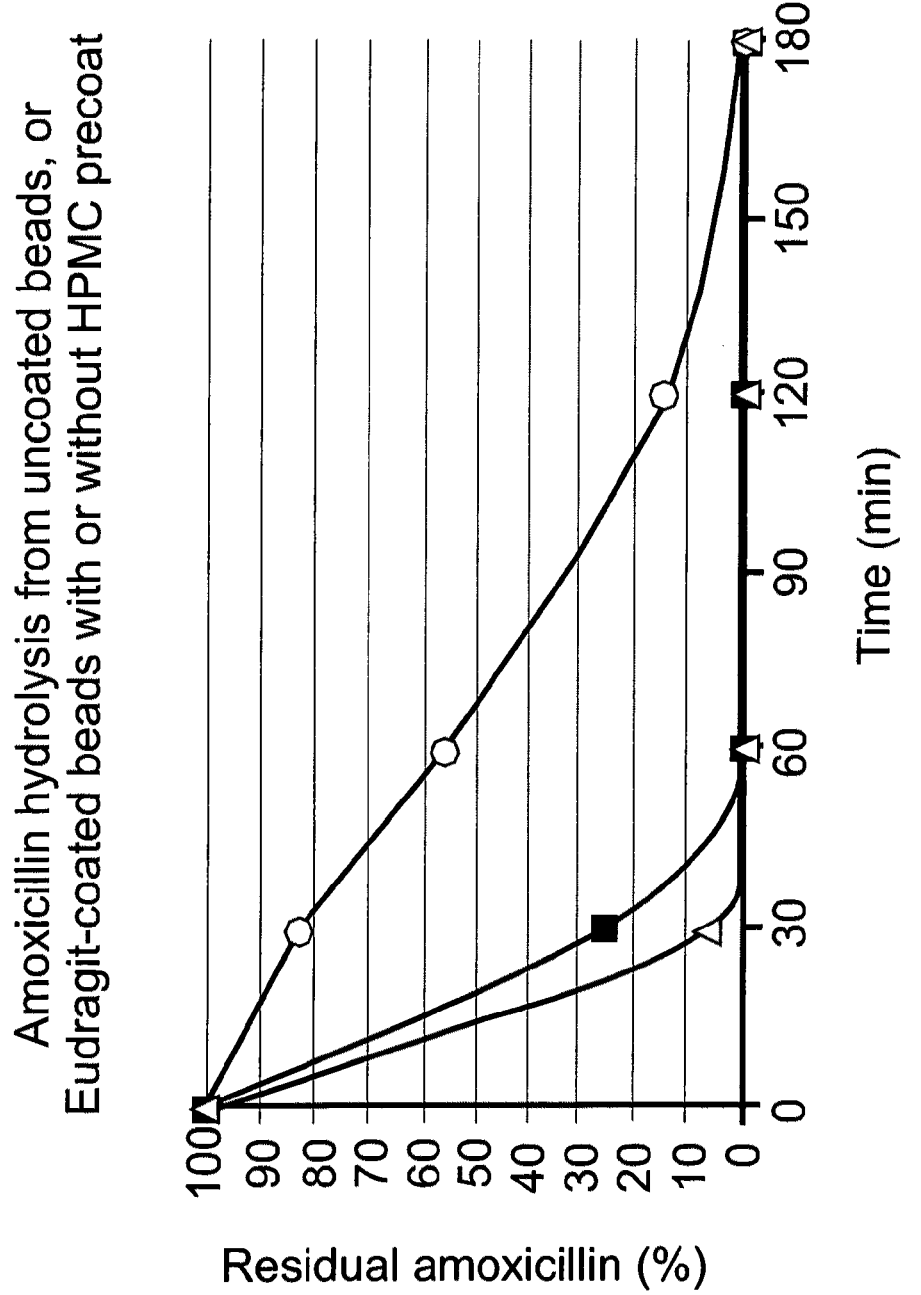
FIG. 6 is a chart showing the hydrolysis of amoxicillin by uncoated, and. Eudragit-coated beads with or without a hydroxypropyl methylcellulose (HPMC) pre-coating, measured in terms of residual amoxicillin (%) versus time (minutes). Blue. triangles represent uncoated beads; red circles represent beads coated with 40% Eudragit L30D-55 without pre-coating; green squares represent beads pre-coated with HPMC and coated with Eudragit L30D-55.

The results are shown in FIG. 6.

EXAMPLE 11

Figure 7:
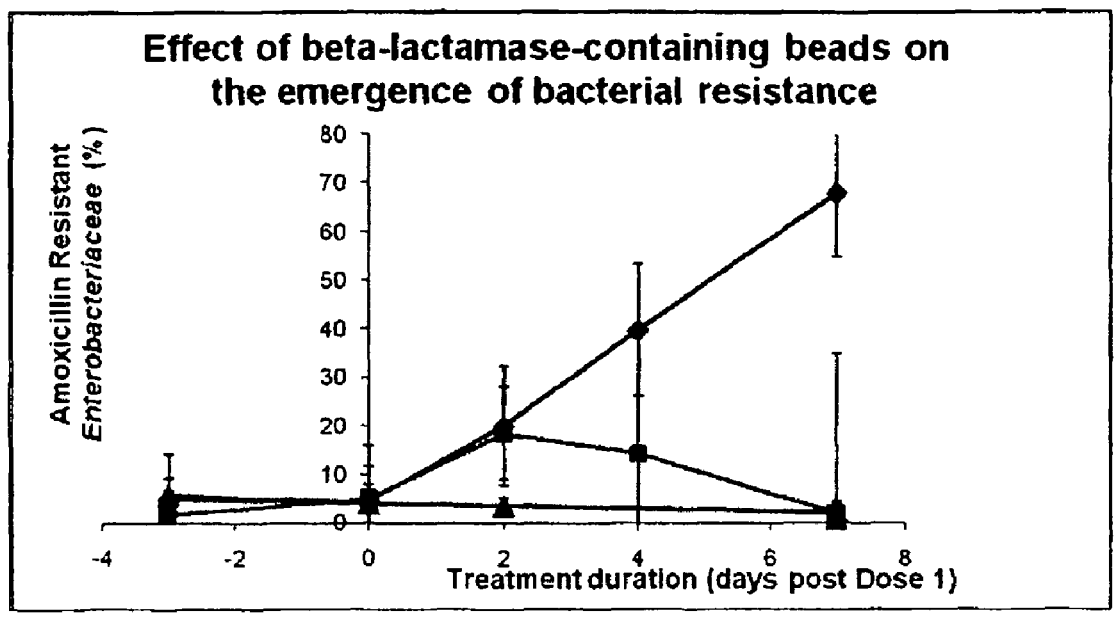
FIG. 7 is a chart showing the effect of Eudragit-coated pectin beads containing β-lactamase L1 on the emergence of antibiotic-resistant bacteria in piglets treated with amoxicillin, measured in terms of amoxicillin resistant bacteriacae (%) versus treatment duration (days). Blue triangles represent untreated animals (n=12); red diamonds represent animals treated with amoxicillin and placebo pectin beads (n=12); green squares represent animals treated with amoxicillin together with Eudragit-coated pectin beads containing β-lactamase L1 (n=4).

Effect of β-lactamase L1 Containing Beads on the Emergence of Bacterial Resistance in Piglets Treated with Amoxicillin 6-7 week old piglets were either untreated, or orally treated with 20 mg/kg amoxicillin per day for 7 days. Half of the treated animals received, together with the daily dose of antibiotics, a gelatin capsule filled with 320 mg pectin beads containing β-lactamase L1, pre-coated with 5% HPMC and coated with 40% Eudragit L30D-55 (batch 100); the other half received similarly coated placebo pectin beads. Feces were collected 3 days before the onset of treatment, and each day during 7 days of treatment and analyzed for their content of total and amoxicillin-resistant enterobacteria on MacConkey agar plates containing 0 or 100 μg/ml amoxicillin. As shown in FIG. 7, the feces of untreated animals contained a minimal proportion of amoxicillin-resistant bacteria (<5%), whereas this proportion rapidly increased in animals treated with amoxicillin, reaching a value between 50 and 80% after 7 days. In contrast, animals receiving β-lactamase containing beads together with amoxicillin only exhibited a transient and limited increase in antibiotic-resistant bacteria. This experiment shows that the co-administration of Eudragit-coated pectin beads containing β-lactamase L1 protected piglets against the emergence of antibiotic resistant bacteria induced by the treatment of animals with amoxicillin.

All patents and publications disclosed herein are incorporated by reference in their entirety. Modifications and variations of the present invention will be obvious to those skilled in the art from the foregoing detailed description of the invention.

The invention claimed is:

1. A colonic drug delivery system comprising pectin beads encapsulating an agent which inactivates an antibiotic, wherein the pectin beads are crosslinked with zinc ions and the pectin beads are coated with a Eudragit® polymer or a mixture of Eudragit® polymers, wherein the agent which inactivates an antibiotic is a beta-lactamase enzyme or an enzyme that inactivates an antibiotic other than a beta-lactam antibiotic.

2. The drug delivery system of claim 1, wherein the agent which inactivates an antibiotic is a beta-lactamase.

3. The drug delivery system of claim 1, wherein the agent which inactivates an antibiotic is beta-lactamase L1 from *Stenotrophomonas maltophilia*.

4. The drug delivery system of claim 1, wherein the agent which inactivates an antibiotic is an erythromycin esterase.

5. The drug delivery system of claim 1, wherein the agent which inactivates an antibiotic is an enzyme that inactivates a quinolone antibiotic.

6. The drug delivery system of claim 1, wherein the agent which inactivates an antibiotic is an enzyme that inactivates a fluoroquinolone antibiotic.

7. The drug delivery system of claim 1, wherein the agent which inactivates an antibiotic is an enzyme that inactivates a glycopeptide antibiotic.

8. The drug delivery system of claim 1, wherein the Eudragit® polymer is selected from the group consisting of Eudragit® L, S, FS, and E polymers with acidic or alkaline groups, and Eudragit® polymers that enable pH-dependent release of the agent.

9. The drug delivery system of claim 1, wherein the Eudragit® polymer is selected from the group consisting of Eudragit® RL and RS polymers with alkaline groups and EUDRAGIT® NE polymers with neutral groups, and Eudragit® polymers that enable controlled time release of the agent by pH-independent swelling.

10. The drug delivery system of claim 1, wherein the mixture of Eudragit® polymers is selected from the group consisting of Eudragit® L, S, FS, and E polymers with acidic or alkaline groups, Eudragit® polymers that enable pH-dependent release of the agent, Eudragit® RL and RS polymers with alkaline groups, EUDRAGIT® NE polymers with neutral groups, and Eudragit® polymers that enable controlled time release of the agent by pH-independent swelling.

11. A method of inactivating an antibiotic in the colon of a patient, comprising administering the drug delivery system of claim 1 to a patient before, during, or after administration of the antibiotic.

12. The method of claim 11, wherein the antibiotic is a beta-lactam containing antibiotic.

13. The method of claim 12, wherein the drug delivery system encapsulates beta-lactamase L1 from *Stenotrophomonas maltophilia*.

14. The method of claim 11, wherein the antibiotic is erythromycin.

15. The method of claim 14, wherein the drug delivery system encapsulates erythromycin esterase.

16. The method of claim 11, wherein the antibiotic is a quinolone.

17. The method of claim 16, wherein the drug delivery system encapsulates an enzyme which activates a quinolone antibiotic.

18. The method of claim 11, wherein the antibiotic is a fluoroquinolone

19. The method of claim 18, wherein the drug delivery system encapsulates an enzyme which activates a fluoroquinolone antibiotic.

20. The method of claim 11, wherein the antibiotic is a glycopeptide.

21. The method of claim 20, wherein the drug delivery system encapsulates an enzyme which activates a glycopeptide antibiotic.

22. The drug delivery system of claim 1, in the form of a tablet, pill, capsule, or gel-cap.

23. The drug delivery system of claim 1, wherein the agent that inactivates an antibiotic is a metallo-dependent enzyme, wherein the metal cation on which the enzyme depends is zinc, and wherein the metallo-dependent enzyme inactivates a beta-lactam antibiotic or an antibiotic other than a beta-lactam antibiotic.

24. The drug delivery system of claim 23, wherein the metallo-dependent enzyme is beta-lactamase L1 from *Stenotrophomonas maltophilia*.

25. The drug delivery system of claim 23, wherein the Eudragit® polymer is selected from the group consisting of Eudragit® L, S, FS, and F polymers with acidic or alkaline groups, and Eudragit® polymers that enable pH-dependent release of the agent.

26. The drug delivery system of claim 23, wherein the Eudragit® polymer is selected from the group consisting of Eudragit® RL and RS polymers with alkaline groups and Eudragit® NE polymers with neutral groups that enable controlled time release of the agent by pH-independent swelling.

27. The drug delivery system of claim 23, wherein the mixture of Eudragit® polymers is selected from the group consisting of Eudragit® L, S, FS, and E polymers with acidic or alkaline groups, Eudragit® polymers that enable pH-dependent release of the active agent, Eudragit® RL and RS polymers with alkaline groups, Eudragit® NE polymers with neutral groups, and Eudragit® polymers that enable controlled time release of the agent by pH-independent swelling.

* * * * *